(12) United States Patent
Bertomeu Asategui

(10) Patent No.: US 10,046,071 B2
(45) Date of Patent: Aug. 14, 2018

(54) CONTINUOUS STERILIZING SYSTEM

(71) Applicant: SURDRY, S.L., Abadino (Vizcaya) (ES)

(72) Inventor: Jose Vicente Bertomeu Asategui, Abadino (ES)

(73) Assignee: SURDRY, S.L., Abadino (Vizcaya) (ES)

( * ) Notice: Subject to any disclaimer, the term of this patent is extended or adjusted under 35 U.S.C. 154(b) by 42 days.

(21) Appl. No.: 15/113,087

(22) PCT Filed: Feb. 13, 2014

(86) PCT No.: PCT/ES2014/070111
§ 371 (c)(1),
(2) Date: Jul. 21, 2016

(87) PCT Pub. No.: WO2015/121511
PCT Pub. Date: Aug. 20, 2015

(65) Prior Publication Data
US 2017/0007729 A1 Jan. 12, 2017

(51) Int. Cl.
| | |
|---|---|
| *A61L 9/00* | (2006.01) |
| *A61L 2/00* | (2006.01) |
| *A01J 11/04* | (2006.01) |
| *A61L 2/04* | (2006.01) |
| *A23L 3/04* | (2006.01) |
| *A23L 3/02* | (2006.01) |

(Continued)

(52) U.S. Cl.
CPC ............ *A61L 2/04* (2013.01); *A23L 3/02* (2013.01); *A23L 3/04* (2013.01); *A61L 2/0023* (2013.01); *B65B 55/14* (2013.01); *B65B 55/18* (2013.01); *A23V 2002/00* (2013.01); *A61L 2202/122* (2013.01); *A61L 2202/21* (2013.01); *A61L 2202/24* (2013.01)

(58) Field of Classification Search
CPC ........................................................ A23L 3/00
USPC ........................... 422/292, 307–308; 99/467
See application file for complete search history.

(56) References Cited

U.S. PATENT DOCUMENTS

| | | |
|---|---|---|
| 662,607 A | 11/1900 | Steinmetz |
| 4,346,650 A | 8/1982 | Zaitsu |

(Continued)

FOREIGN PATENT DOCUMENTS

| | | |
|---|---|---|
| EP | 0304655 A2 | 3/1989 |
| EP | 0692196 A1 | 1/1996 |

(Continued)

OTHER PUBLICATIONS

International Search Report dated Oct. 28, 2014 for PCT/ES2014/070111 and English translation.

*Primary Examiner* — Monzer R Chorbaji
(74) *Attorney, Agent, or Firm* — Lucas & Mercanti, LLP

(57) ABSTRACT

The invention relates to a continuous sterilizing system comprising a sterilizing body into which a thermal fluid is introduced for sterilizing products, the products to be sterilized being arranged in containers that circulate inside the sterilizing body, said sterilizing body being divided into different sterilization zones by means of dividing walls, and each of said dividing walls having a through-opening that is substantially the same shape as a container, such that the containers close the through-openings of the dividing walls, rendering the sterilization zones thermally isolated from one another.

14 Claims, 5 Drawing Sheets

(51) Int. Cl.
*B65B 55/14* (2006.01)
*B65B 55/18* (2006.01)

(56) References Cited

U.S. PATENT DOCUMENTS

| | | | |
|---|---|---|---|
| 4,666,722 A * | 5/1987 | Creed | ............... A23L 3/362 |
| | | | 426/393 |
| 4,827,727 A | 5/1989 | Caracciolo | |
| 5,160,755 A | 11/1992 | Mignogna et al. | |

FOREIGN PATENT DOCUMENTS

| | | | |
|---|---|---|---|
| ES | 466875 | A1 | 10/1978 |
| ES | 2345060 | T3 | 9/2010 |
| ES | 2362515 | A1 | 7/2011 |

* cited by examiner

CONTINUOUS STERILIZING SYSTEM

CROSS REFERENCE TO RELATED APPLICATIONS

This Application is a 371 of PCT/ES2014/070111 filed on Feb. 13, 2014, application which is incorporated herein by reference.

FIELD OF THE ART

The present invention relates to pieces of equipment used for sterilizing or pasteurizing food products, pharmaceutical products, or the like.

STATE OF THE ART

Products such as packaged foods, medical and surgical instruments or pharmaceutical products are sterilized or pasteurized inside pieces of equipment provided with tight closure in which a thermal fluid, such as steam, air or water, is applied under specific temperature and pressure conditions.

To perform this process, aseptic systems are known in which the products are sterilized before being packaged. These systems are generally used for rapid sterilization of liquid products with low solids load, such as for example, milk. For products with higher solids load, in which a longer time is required to obtain a suitable sterilization, discontinuous systems and continuous systems are known, in which the products are sterilized after packaging.

Discontinuous systems, such as for example, the system proposed by Spanish patent ES2362515 belonging to the same applicant as the present invention, relates to pieces of equipment in which the products are sterilized in batches. These pieces of equipment are not suitable for large series of products and long successive production hours, because when a new batch of products is to be sterilized the equipment must be depressurized and cooled for subsequently pressurizing and heating the equipment again to enable sterilizing the next batch of products, with the time loss and energy expenditure it entails.

Continuous systems allow sterilizing large series of products optimizing time and energy expenditure, in addition to improving the quality and safety of the treated product. These systems are usually formed by vertical sterilization towers or large horizontal autoclaves, the products to be sterilized being circulated inside them. Patent documents EP304655, U.S. Pat. No. 5,160,755, or U.S. Pat. No. 662,607 disclose some continuous sterilization systems.

Specifically, European patent EP304655 discloses an apparatus for sterilizing food products that are arranged in moving cars circulating inside a sterilizing chamber in which a thermal fluid is injected for treatment of the products. The sterilizing apparatus has a pressurizing chamber through which the moving cars are introduced into the sterilizing chamber and a depressurizing chamber through which the moving cars with the now sterilized products are removed from the sterilizing chamber. The sterilizing chamber has a system with deflectors for distributing the thermal fluid which allows establishing zones with different temperatures inside the sterilizing chamber.

The temperature difference between zones which can be obtained with the deflectors is limited, there is no suitable thermal insulation between zones, the temperature provided by the thermal fluid being easily transmitted from one zone to another contiguous zone of the sterilizing chamber.

A piece of continuous sterilizing equipment having suitable thermal insulation between zones for optimizing the energy consumption and processing time of the products to be sterilized is therefore necessary.

OBJECT OF THE INVENTION

The present invention proposes a piece of continuous sterilizing equipment for sterilizing or pasteurizing food products, pharmaceutical products, or the like.

The continuous sterilizing equipment object of the invention comprises a sterilizing body into which a thermal fluid, such as hot water or steam, is introduced thereby sterilizing or pasteurizing the products. The food products, pharmaceutical products, or the like to be treated are arranged in containers that are circulated inside the sterilizing body in which they are treated.

In the sense of the invention, a container is a substantially cubic-shaped element involving a series of receptacles, generally in the form of rectangular trays, the products to be treated by the sterilizing equipment being incorporated inside the receptacles. It has been envisaged that the container is formed by a vertical stack of receptacles, although it may also be possible that the container is a structure in the form of a rack-type cupboard or the like with multiple housings in which the receptacles are arranged.

The sterilizing body is divided by means of dividing walls in different sterilization zones through which the containers with the products to be treated are circulated. Each sterilization zone of the sterilizing body has an individual thermal fluid supply, such that each sterilization zone has a working temperature independent of the other sterilization zones.

Each dividing wall has a through hole having a shape substantially identical to the shape of a container, such that the containers themselves close the through holes of the dividing walls, the sterilization zones therefore being thermally isolated from one another.

The height and width of the through hole of a dividing wall is substantially identical to the height and width of a container. Likewise, the possibility that the depth of a container is slightly greater than the distance between two contiguous dividing walls has been envisaged, such that one and the same container partially enters the through holes of two contiguous dividing walls, one and the same container therefore closing the through holes of two dividing walls.

The receptacles forming the containers and holding the products to be sterilized incorporate a thermal insulation layer which is arranged at least in the front part of the receptacles according to the direction of forward movement of the receptacles inside the sterilizing body, although the thermal insulation layer can be arranged in the front part and in the rear part of the receptacles.

According to one embodiment of the invention, receptacles are introduced into the sterilizing body, the containers being formed inside the sterilizing body itself by means of a vertical stack of receptacles. Therefore, according to this embodiment the sterilizing body incorporates an inlet for the introduction of receptacles and an outlet for the removal of receptacles. It has been envisaged that the receptacles are introduced and removed individually, although they could be introduced and removed in groups of two or more receptacles.

According to another embodiment of the invention, the containers are formed outside the sterilizing body. Therefore, according to this embodiment the sterilizing body incorporates an inlet for the individual introduction of containers into the sterilizing body and an outlet for the individual removal of containers from the sterilizing body.

For the purpose of optimizing the space taken up by the sterilizing equipment, and in the case of introducing the receptacles individually into the sterilizing body and forming containers therein, it has been envisaged that the inlet and outlet of the sterilizing body are arranged on the same side of the sterilizing body. In the case of introducing containers that are formed outside the sterilizing body, it has been envisaged that the inlet and outlet of the sterilizing body are aligned with the sterilizing body, the inlet being arranged at the front of the sterilizing body and the outlet being arranged at its rear part. In any case, and without altering the object of the invention, the inlet and outlet of the sterilizing body can be arranged on the same side of the sterilizing body, on opposing sides, or aligned with the sterilizing body, the inlet and outlet having a size consistent with the receptacles or containers to be introduced.

In relation to the inlet and outlet of the sterilizing body there is arranged a respective pressurizing chamber which could be filled with water to reduce the pressure rise and drop time, and therefore the time for loading receptacles in the sterilizing equipment and unloading them.

The sterilizing body has at one of its ends a loading zone for containers, and at the opposite end an unloading zone for containers. In the case of introducing receptacles into the sterilizing body to form containers therein, the loading zone has lifting and lowering means for vertically stacking the receptacles and forming containers, and the unloading zone has other lifting and lowering means for separating the containers and removing the receptacles out of the sterilizing body.

The sterilizing body has in its lower part drive means, such as drive chains, conveyor belts or the like, for moving the containers through the loading zone, the sterilization zones and the unloading zone. The drive means can be made up of a single drive element common for the loading zone, the sterilization zones and the unloading zone, or can be made up of several drive elements, an independent drive element being arranged for each zone of the sterilizing body.

A piece of continuous sterilizing equipment is thereby obtained which, as a result of its constructive and functional features, is preferably applicable for thermal treatment of food products, pharmaceutical products, or the like, which assures suitable thermal insulation between the different sterilization zones, optimizing energy consumption and reducing the processing time of the products to be sterilized.

DESCRIPTION OF THE DRAWINGS

FIG. 1A shows a perspective view of a container with stacked receptacles in which the products to be sterilized are arranged.

DETAILED DESCRIPTION OF THE INVENTION

Figure 1:
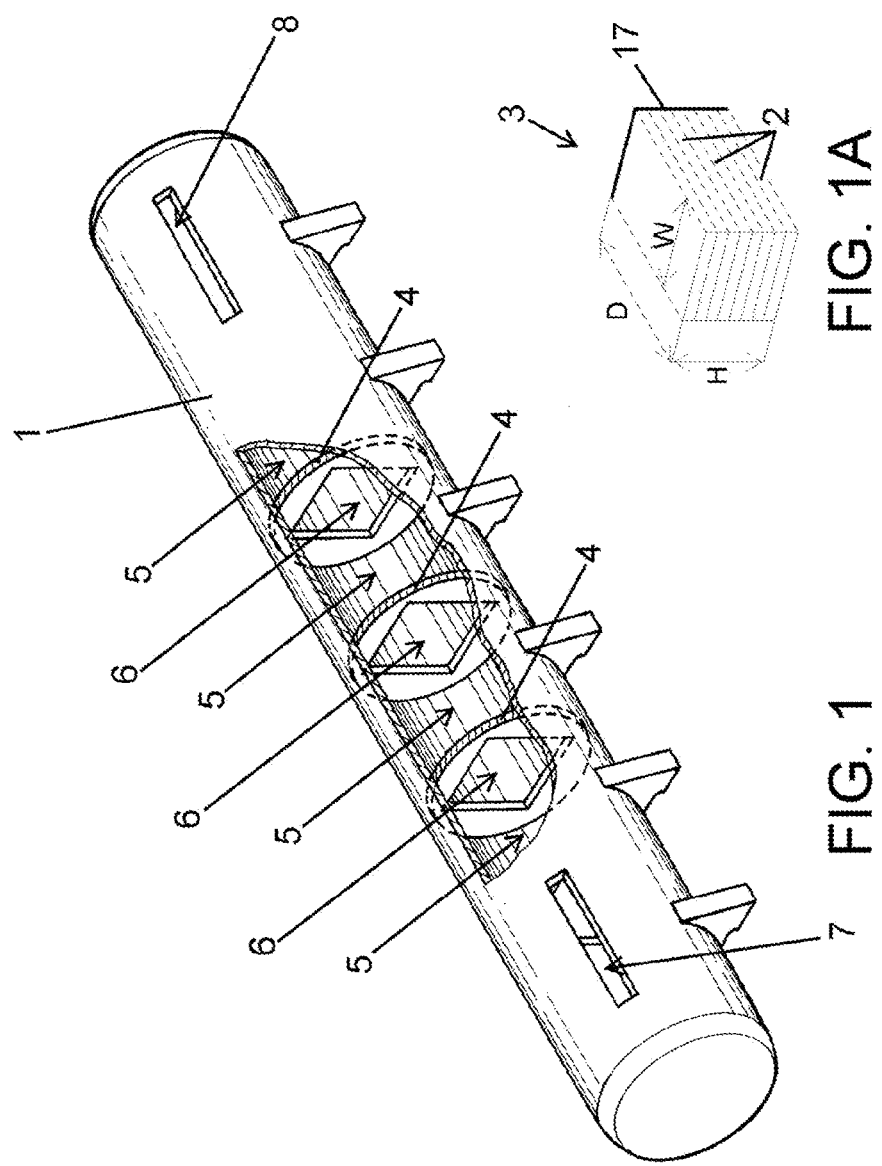
FIG. 1 shows a perspective view with a partial section of the sterilizing equipment according to one embodiment of the invention.

FIG. 1 shows a perspective view of a possible embodiment of the continuous sterilizing equipment object of the invention. The sterilizing equipment is made up of a substantially cylindrical sterilizing body (1) into which a thermal fluid, such as hot water or steam, is injected, creating pressure and temperature conditions suitable for sterilizing or pasteurizing products which are arranged therein.

The products to be treated by the sterilizing equipment are arranged inside receptacles (2). As seen in the example of FIG. 1A, the receptacles (2) are in the form of rectangular trays which are stacked vertically to form containers (3) that are moved inside the sterilizing body (1). The stack of receptacles (2) can be formed inside the sterilizing body (1), according to the embodiment of the invention depicted in FIGS. 1 to 5, or can be formed outside the sterilizing body, according to the embodiment shown in FIG. 6.

The sterilizing equipment has dividing walls (4) arranged transversely along the inside of the sterilizing body (1). The dividing walls (4) divide the sterilizing body (1) in different sterilization zones (5) that are thermally isolated from one another, such that each sterilization zone (5) is at a temperature and a step of thermal treatment of one of the containers (3) circulating inside the sterilizing body (1) takes place therein.

Each dividing wall (4) has a through hole (6) with a shape substantially identical to a container (3), such that the container (3) itself closes the through hole (6) of a dividing wall (4), thermally insulating two contiguous sterilization zones (5) of the sterilizing body (1).

Figure 2:
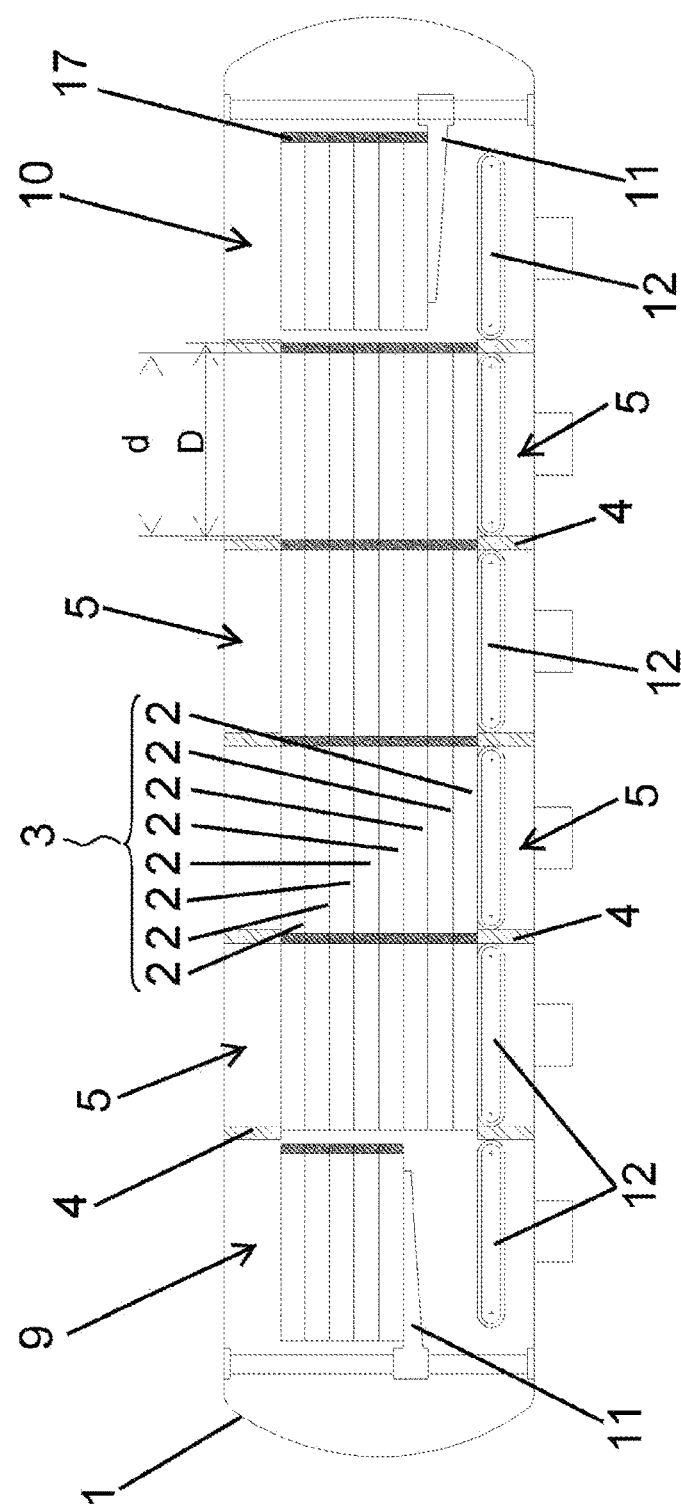
FIG. 2 is an elevational view with a longitudinal section showing the inside of the sterilizing equipment depicted in FIG. 1.
Figure 3:
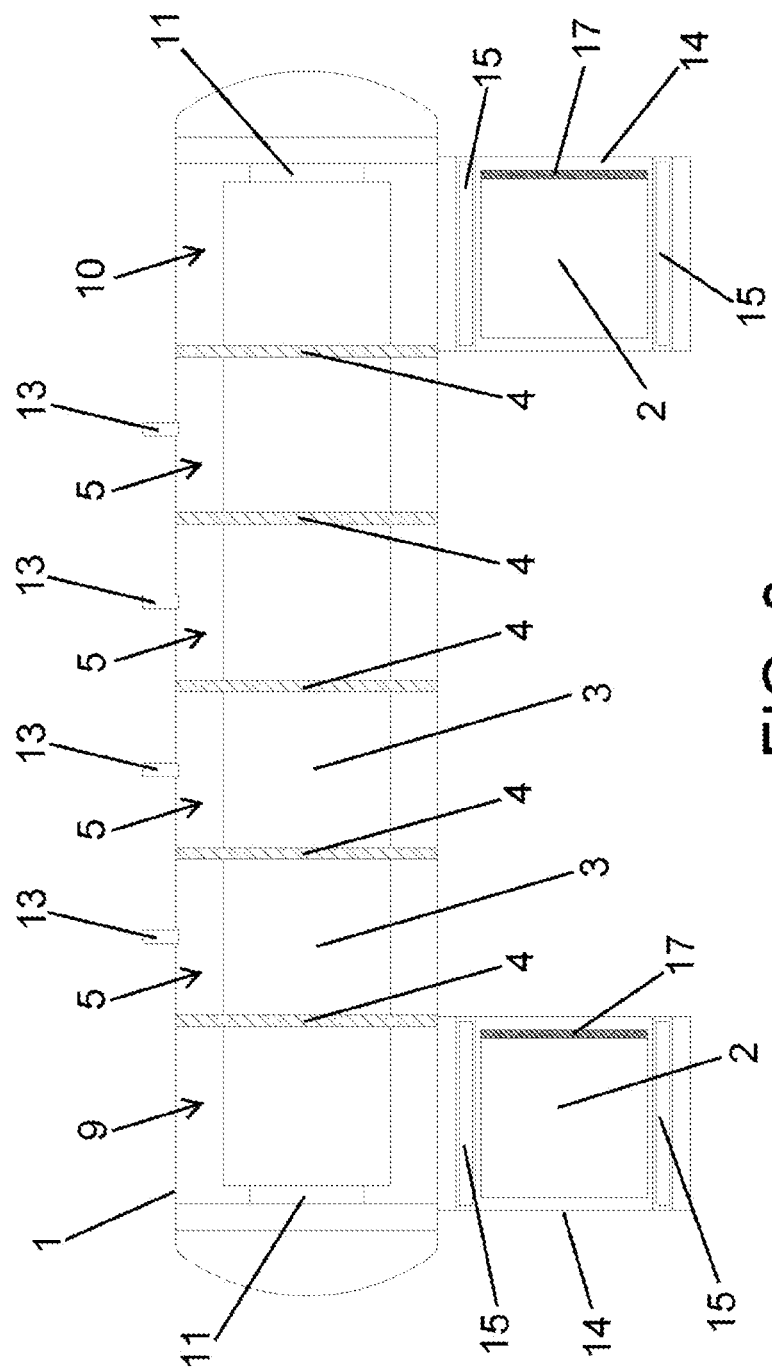
FIG. 3 is a plan view of the sterilizing equipment of FIG. 1 in which the pressurizing chambers for product entry and exit are shown.
Figure 4:
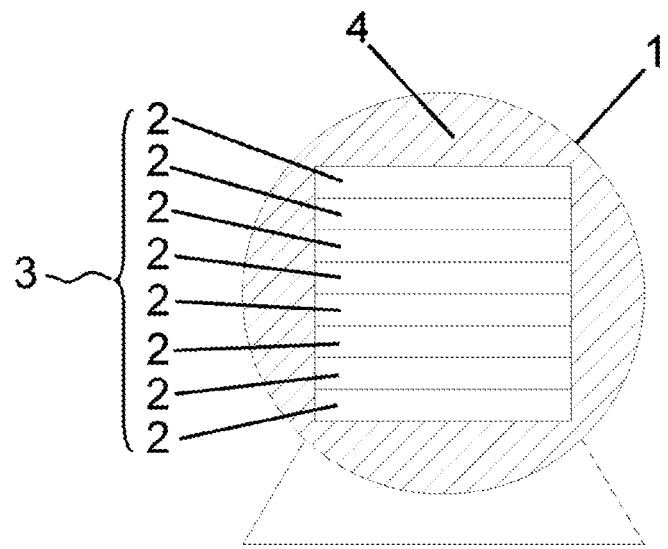
FIG. 4 shows a cross-section view of the sterilizing equipment in which one of the dividing walls inside the sterilizing body is observed.

As seen in the embodiments shown in the drawings, the height (H) and width (W) of a container (3) is substantially identical to the height and width of a through hole (6) of a dividing wall (4), such that the outer contour of the container (3) contacts the through hole (6) closing it. Likewise, and as can be seen in the embodiment of FIG. 2 it has been envisaged that each container (3) has a depth (D) slightly greater than the distance (d) between two contiguous dividing walls (4), such that one and the same container (3) partially enters the through holes (6) of two contiguous dividing walls (4), therefore closing both dividing walls (4). Nevertheless, the depth (D) of the containers (3) can be less than the distance (d) between dividing walls (4), in which case the stacked containers (3) move inside the sterilizing body (1) in a contiguous row without there being a gap between them, assuring in that case that the through holes (6) of the dividing walls (4) are suitably closed, and preventing the temperature of a sterilization zone (5) from being transmitted to the contiguous sterilization zones (5).

According to the embodiment of the invention depicted in FIGS. 1 to 5, the receptacles (2) with the products to be sterilized are introduced into and removed from the sterilizing body (1) individually, such that as seen in FIG. 1, the sterilizing body (1) has at one of its ends an inlet (7) through which the receptacles (2) with the products to be sterilized are introduced, and has at the opposite end an outlet (8) through which the receptacles (2) with the now sterilized products are removed. It may also be possible that the receptacles (2) are introduced into and removed from the sterilizing body (1) in groups of two or more receptacles (2), in which case the inlet (7) and outlet (8) of the sterilizing body (1) are adapted to the size of the group of receptacles (2).

According to the embodiment shown in FIGS. 1 to 5, for the sterilizing equipment to take up as little space as possible in the plant in which it will be located, it has been envisaged that the inlet (7) and outlet (8) of the sterilizing body (1) are arranged on one and the same side of the sterilizing body (1), although depending on the needs in the plant, the inlet (7) and outlet (8) of the sterilizing body (1) can be located in other positions, for example, the inlet (7) can be located on one side of the sterilizing body (1) and the outlet (8) on the opposing side, or the inlet (7) can be located in the front part of the sterilizing body (1) and the outlet (8) in the rear part thereof.

In relation to the inlet (7), the sterilizing body (1) has therein a loading zone (9) for containers (3), whereas in relation to the outlet (8), the sterilizing body (1) has therein an unloading zone (10) for containers (3).

According to the embodiment of the invention shown in FIGS. 1 to 5, where the receptacles (2) are individually introduced into and removed from the sterilizing body (1), and as seen in detail in FIG. 2, the loading zone (9) of the sterilizing body (1) has lifting and lowering means (11) for vertically conveying the receptacles (2) and forming a container (3) inside the sterilizing body (1), whereas the unloading zone (10) has other lifting and lowering means (11) which likewise allow the vertical movement of a container (3) for gradually removing receptacles (2) that have been sterilized from the sterilizing body (1). It has been envisaged that the lifting and lowering means (11) are a lifting platform, although they could be vertical drive chains or any other lifting system allowing vertical movement of the receptacles (2).

Figure 6:
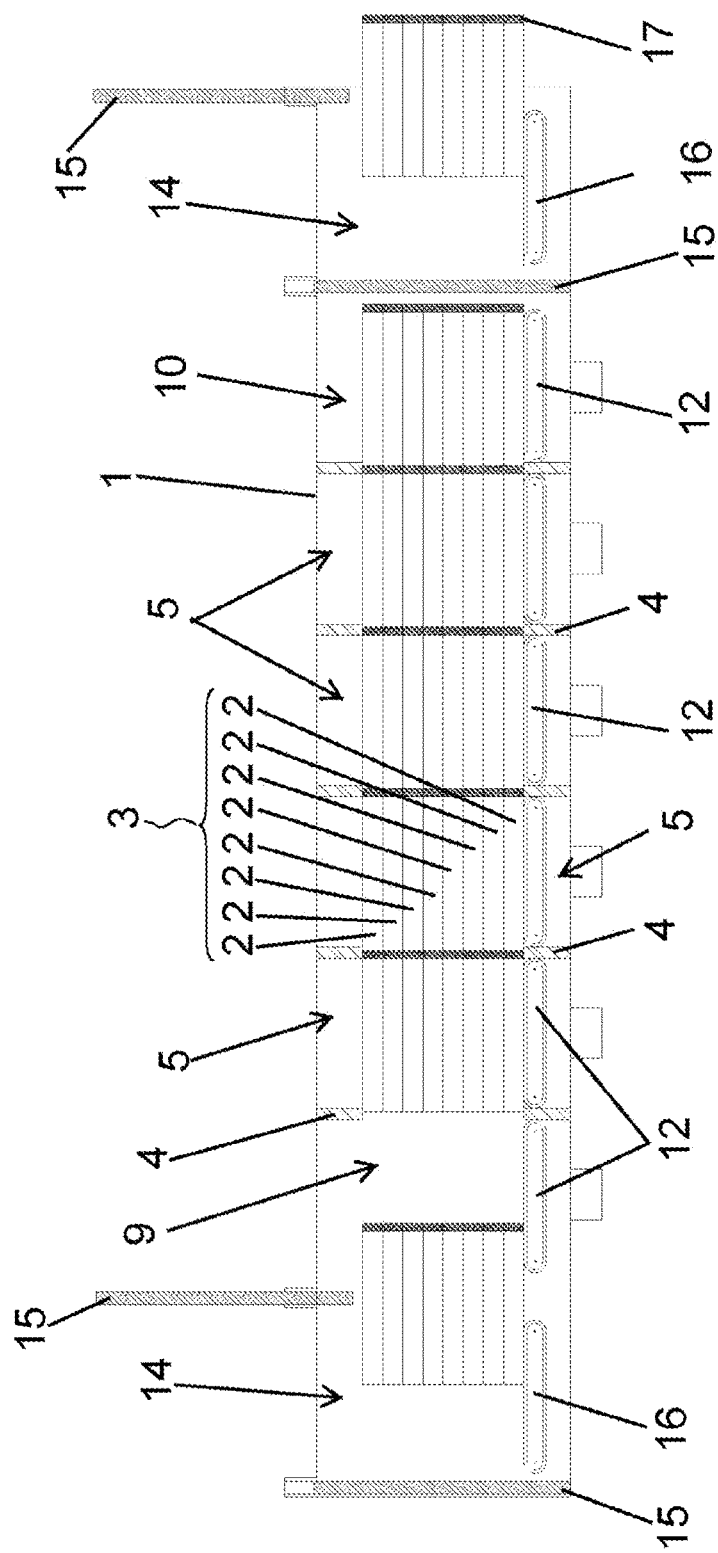
FIG. 6 shows an elevational view with a longitudinal section of the inside of a piece of sterilizing equipment according to another embodiment of the invention.

As seen in the embodiment of the invention shown in FIG. 6, the loading zone (9) and unloading zone (10) do not have lifting and lowering means (11) because the containers (3) with receptacles (2) are formed outside the sterilizing body (1), the containers (3) being wholly introduced into and removed from the sterilizing body (1).

The sterilizing equipment has drive means (12) for moving the containers (3) along the successive sterilization zones (5) inside the sterilizing body (1). The drive means (12) can be formed by horizontal drive chains, conveyor belts or any similar conveyance system. The drive means (12) are arranged in the lower part of the sterilizing body (1) and can be continuous means formed by a single drive element common for all the sterilization zones (5) and the loading zone (9) and unloading zone (10), or as depicted in the embodiments of the drawings, they can be discontinuous means formed by several drive elements, such that each sterilization zone (5) and the loading zone (9) and unloading zone (10) have respective drive elements.

Each sterilization zone (5) of the sterilizing body (1) has an individual thermal fluid supply (13), such that by controlling the temperature and flow rate of the supplied thermal fluid the working temperature of each sterilization zone (5) is controlled. It has been envisaged that the sterilization zones (5) are interconnected to one another by means of a system of ducts and valves for recirculating the thermal fluid between the various sterilization zones (5) when necessary, optimizing energy efficiency.

Since the sterilizing body (1) is subjected to pressure for sterilizing the products, the receptacles (2) are loaded into and unloaded from the sterilizing body (1) through pressurizing chambers (14) adapting the pressure inside the sterilizing body (1) to the atmospheric pressure outside. Therefore, a respective pressurizing chamber (14) is arranged in connection with the inlet (7) and the outlet (8). The pressurizing chambers (14) can be filled with water to reduce the pressure rise and drop time, therefore also preventing the use of complex air compression pumps.

Figure 5:
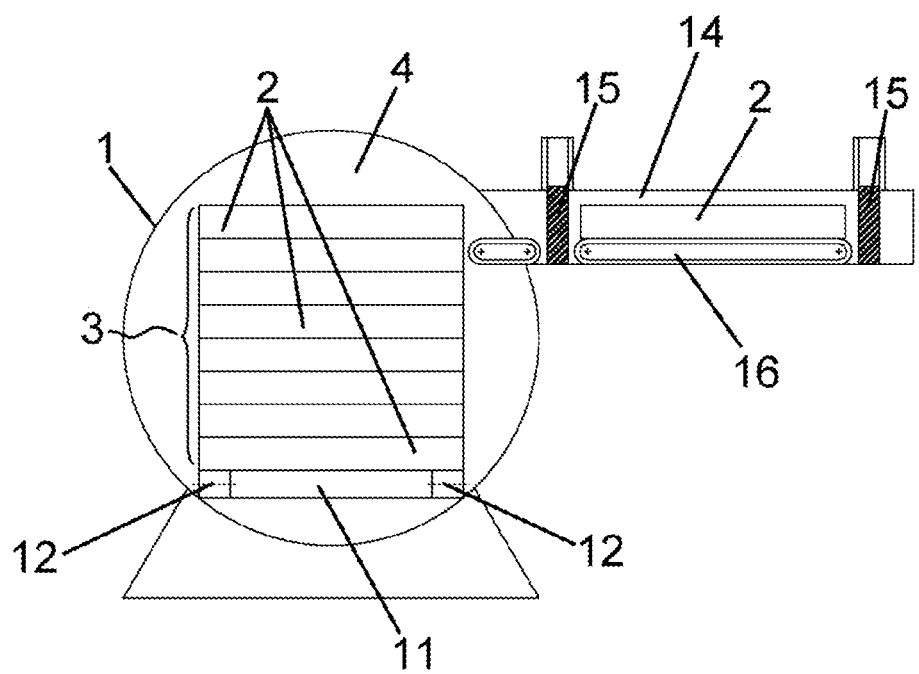
FIG. 5 shows another cross-section view of the sterilizing equipment in which one of the pressurizing chambers is shown.

As seen in FIG. 5, each pressurizing chamber (14) has opening and closing locks (15), gates or the like, of a reduced size similar to that of a receptacle (2), such that it allows reducing the time used for increasing or lowering the pressure of the pressurizing chamber (14) and optimizing energy consumption. Conveying means (16) are arranged in relation to the pressurizing chamber (14) to enable moving the receptacles (2) through the pressurizing chambers (14) while loading the receptacles (2) into the sterilizing body (1) and unloading them, therefore the receptacles (2) themselves could, for example, have wheels in their lower part for moving through the pressurizing chambers (14), or it may also be possible that the pressurizing chamber (14) itself has in its lower part a conveyor belt or another system which allows moving the receptacles (2) inside same.

In the embodiment of the invention shown in FIG. 6 in which the containers (3) made up of receptacles (2) are formed outside the sterilizing body (1), the pressurizing chambers (14) that are used for adapting the pressure inside the sterilizing body (1) to the atmospheric pressure outside have a size similar to that of a container (3). It has been envisaged that the pressurizing chambers are aligned with the sterilizing body (1) at their front and at their rear part, although they could be arranged in another position, such as for example, on the sides of the sterilizing body (1), as is the case of the embodiment of the invention shown in FIGS. 1 to 5.

The receptacles (2) forming the containers (3) incorporate a thermal insulation layer (17) which is arranged at least in the front part of the receptacles (2) in the direction of forward movement thereof, said thermal insulation layer (17) being able to be arranged additionally in the rear part of the receptacles (2). Since the containers (3) circulate continuously inside the sterilizing body (1), the thermal insulation layer (17) allows preventing the temperature to which a container (3) is being subjected from being transmitted to the container (3) arranged immediately before or after, likewise the thermal insulation layer (17) improves the sealing of the through holes (6) of the dividing walls (4), improving the thermal insulation between the sterilization zones (5) of the sterilizing body (1).

Therefore, this being the case and according to the embodiment of FIGS. 1 to 5, in order to sterilize products the sterilizing body (1) is first pressurized at the working temperature, the products to be sterilized are introduced into the receptacles (2), and the receptacles (2) are individually introduced into the pressurizing chamber (14) linked to the inlet (7) of the sterilizing body (1) so that the receptacles (2) are gradually positioned on the lifting and lowering means (11) of the loading zone (9).

Receptacles (2) are therefore gradually introduced into the loading zone (9) until a first container (3) is formed, which once formed goes to the first sterilization zone (5). Next, while the first container (3) is being treated in the first sterilization zone (5), a second container (3) is being formed in the loading zone (9). When treatment of the first container (3) in the first sterilization zone (5) has ended, it goes to the second sterilization zone (5), and the second container (3) which was in the loading zone (9) moves to the first sterilization zone (5) to start treatment. Therefore, the containers (3) gradually go through the different sterilization zones (5) until they reach the unloading zone (10), in which the receptacles (2) are removed through the pressurizing chamber (14) of the outlet (8) of the sterilizing body (1).

Therefore, each sterilization zone (5) always works at the same temperature for each cycle of product to be treated, such that it is not necessary to heat and cool the sterilizing equipment every time a new batch of products is to be processed, optimizing energy consumption. As a general rule, during product treatment the temperature increases progressively in the first sterilization zones (5), the maximum treatment temperature corresponding with the sterilization zone (5) arranged in the center of the sterilizing body (1), and then the it decreases progressively in the following sterilization zones (5).

In the embodiment of FIG. 6, product sterilization is completely identical with the exception that the receptacles (2) are introduced into the sterilizing body (1) after they are already stacked into containers (3).

The drawings show a piece of sterilizing equipment (1) with four sterilization zones (5), although the number of sterilization zones (5) will depend on the type of products to be sterilized, having as many sterilization zones (5) as needed for a correct product treatment. Likewise, the possibility of arranging several pieces of continuous sterilizing equipment each working at different pressure when the type of product to be treated so requires is contemplated.

The sterilizing equipment has been depicted in the drawings in a horizontal arrangement, although it could be arranged vertically without it altering the concept of the invention.

The invention claimed is:

1. A piece of continuous sterilizing equipment comprising:
   a sterilizing body into which a thermal fluid is introduced for sterilizing products, the products to be sterilized being arranged in containers circulating inside the sterilizing body, the containers having a selected shape; and
   a plurality of dividing walls disposed inside the sterilizing body, the plurality of dividing walls defining a plurality of sterilization zones within the sterilizing body, wherein each dividing wall includes a hole having a shape substantially identical to the selected shape of the containers, such that the containers close the holes in the plurality of dividing walls, causing the sterilization zones to be thermally isolated from one another,
   wherein each container comprises a vertical stack of receptacles, and
   wherein the sterilizing body includes an inlet for introducing receptacles, and an outlet for removing receptacles.

2. The continuous sterilizing equipment according to claim 1, wherein a first pressurizing chamber is arranged in relation to the inlet and a second pressurizing chamber is arranged in relation to the outlet.

3. The continuous sterilizing equipment according to claim 2, wherein the first and second pressurizing chambers can be filled with water to reduce pressure rise and drop time.

4. The continuous sterilizing equipment according to claim 1, wherein the sterilizing body has at a first end a loading zone for containers, and the sterilizing body has at a second end an unloading zone for containers.

5. The continuous sterilizing equipment according to claim 4, wherein the loading zone has lifting and lowering means for forming containers inside the sterilizing body by means of vertically stacking receptacles that are introduced into the sterilizing body, and the unloading zone has other lifting and lowering means for separating the container and removing the receptacles out of the sterilizing body.

6. The continuous sterilizing equipment according to claim 4, wherein the sterilizing body has a drive means for moving the containers through the loading zone, the sterilization zones and the unloading zone.

7. The continuous sterilizing equipment according to claim 6, wherein the drive means includes a single drive element common for the loading zone, the sterilization zones and the unloading zone.

8. The continuous sterilizing equipment according to claim 6, wherein the drive means comprises a plurality of drive elements, a respective drive element being arranged for each of the sterilization zone, the loading zone, and the unloading zone.

9. The continuous sterilizing equipment according to claim 1, wherein a height and a width of a hole of a dividing wall is substantially identical to the height (H) and width (W) of a container.

10. The continuous sterilizing equipment according to claim 1, wherein the depth (D) of a container is slightly greater than the distance (d) between two contiguous dividing walls, such that one and the same container partially enters the holes of two contiguous dividing walls.

11. The continuous sterilizing equipment according to claim 1, wherein each sterilization zone of the sterilizing body has an individual thermal fluid supply.

12. The continuous sterilizing equipment according to claim 1, wherein the sterilizing body has a horizontal arrangement.

13. The continuous sterilizing equipment according to claim 1, wherein the sterilizing body has a vertical arrangement.

14. The continuous sterilizing equipment according to claim 1, wherein each container is formed by a vertical stack of receptacles, wherein each receptacle incorporates a thermal insulation layer which is arranged at least in the front part of each receptacle according to the direction of forward movement of the container inside the sterilizing body.

* * * * *